United States Patent [19]
Companion

[11] Patent Number: 5,755,571
[45] Date of Patent: May 26, 1998

[54] DIFFERENTIAL MEASUREMENT PERIODONTAL STRUCTURES MAPPING SYSTEM

[75] Inventor: John A. Companion, Hampton, Va.

[73] Assignee: The United States of America as represented by the Administrator of the National Aeronautics and Space Administration, Washington, D.C.

[21] Appl. No.: 712,984

[22] Filed: Sep. 9, 1996

[51] Int. Cl.$^6$ .................................................. A61C 19/04
[52] U.S. Cl. ........................... 433/72; 128/776; 33/514
[58] Field of Search ......................... 433/72, 75, 32; 128/776, 777; 33/513, 514

[56] References Cited

U.S. PATENT DOCUMENTS

| | | | |
|---|---|---|---|
| 4,250,895 | 2/1981 | Lees | 433/72 |
| 4,665,621 | 5/1987 | Ackerman et al. | 33/513 |
| 4,677,756 | 7/1987 | Simon et al. | 33/514 |
| 4,708,647 | 11/1987 | Pippin et al. | 433/32 |
| 4,764,114 | 8/1988 | Jeffcoat et al. | 433/72 |
| 4,823,809 | 4/1989 | Gott, Jr. et al. | 128/776 |
| 4,904,184 | 2/1990 | Murphy et al. | 433/72 |
| 4,947,245 | 8/1990 | Ogawa et al. | 358/98 |
| 5,100,318 | 3/1992 | Demyun et al. | 433/72 |
| 5,197,487 | 3/1993 | Ackerman et al. | 128/776 |
| 5,382,163 | 1/1995 | Putnam | 433/215 |

*Primary Examiner*—Cary E. O'Connor
*Attorney, Agent, or Firm*—Robin W. Edwards

[57] ABSTRACT

This invention relates to a periodontal structure mapping system employing a dental handpiece containing first and second acoustic sensors for locating the Cemento-Enamel Junction (CEJ) and measuring the differential depth between the CEJ and the bottom of the periodontal pocket. Measurements are taken at multiple locations on each tooth of a patient, observed, analyzed by an optical analysis subsystem, and archived by a data storage system for subsequent study and comparison with previous and subsequent measurements. Ultrasonic transducers for the first and second acoustic sensors are contained within the handpiece and in connection with a control computer. Pressurized water is provided for the depth measurement sensor and a linearly movable probe sensor serves as the sensor for the CEJ finder. The linear movement of the CEJ sensor is obtained by a control computer actuated by the prober. In an alternate embodiment the CEJ probe is an optical fiber sensor with appropriate analysis structure provided therefor.

20 Claims, 9 Drawing Sheets

FIG. 9

DIFFERENTIAL MEASUREMENT PERIODONTAL STRUCTURES MAPPING SYSTEM

ORIGIN OF THE INVENTION

The invention described herein was made in the performance of work under a NASA Contract and is subject to the provisions of Section 305 of the National Aeronautics and Space Act of 1958, as amended, Public Law 85-568 (72 Stat. 435; 42 USC 2457).

FIELD OF THE INVENTION

This invention relates generally to measurement systems and relates specifically to a system for differential measurement and mapping of periodontal structures of a dental patient.

BACKGROUND OF THE INVENTION

Periodontal disease is the single most pervasive dental disease, and is the leading cause of tooth loss for adults over 35 years of age. The principal mechanisms by which periodontal disease causes tooth loss are erosion of the periodontal ligament which holds each tooth into its socket and then erosion of the actual bone of the socket so that the tooth gradually loses its supporting structure. The disease typically proceeds from an increased concentration of bacteria in the normal sulcus (pocket) formed where the gingival epithelium folds downward along the tooth face at the abutment point. The sulcus is normally quite shallow and 1–2 mm of depth is not cause for concern. Periodontal disease can be quite localized and is not painful in the early stages. The progression of the disease can cause rapid, localized deepening of the pocket. The pocket will later become inflamed, pus filled, and prone to bleeding when the teeth are brushed or probed by a dentist.

Since the early stages of the disease are painless, many people do not realize that they have it until it is well advanced. Many others find the current state of the art of manual probing to be sufficiently uncomfortable that they put it off until the disease is well advanced. Aggressive treatment is then the only option. A reliable, accurate method which would detect the disease at an early stage and also be less objectionable to the patient would be a real advancement. In the dental research arena there are millions of dollars and hundreds of thousands of man hours presently being dedicated to developing biochemical and microbial tests for periodontal disease activity, but there is no "gold standard" measuring technique for the accurate detection and assessment of the disease.

The space occupied by the periodontal ligament is normally on the order of 0.5 mm wide and is located between the outer surface of the root of the tooth and the inner surface of the bone forming the socket in which the tooth resides. The actual periodontal ligament, which is a dense fibrous tissue, fills the periodontal space and the fibers of which it is composed penetrate pores in both the tooth and the bone surfaces to bond the tooth in place in a slightly resilient manner. The actual crest of the periodontal ligament is normally covered with approximately 1 mm of epithelial tissue which forms the bottom of the periodontal pocket. The dental community has concluded that tracking the recession of the upper boundary of the periodontal ligament over a period of time is a good measure of the progress of periodontal disease.

The primary accepted method for making this measurement in general use today is periodontal probing. In this procedure, the dentist inserts the tip of a graduated metal probe at the juncture of the gingival margin with the face of an individual tooth and pushes it manually down along the root surface. When sufficient resistance is felt, the dentist judges that the periodontal ligament has been reached, the depth of insertion is measured via the tool graduations and recorded onto a printed chart. The dentist is trained to, and assumed to, push the probe into the tissue with a force of 25 grams (although some studies have found that 35 grams produces more accurate results), to insure consistency of the probe readings. In reality, this procedure is highly invasive, uncomfortable for the patient, and subject to a high degree of variability. The desired reference point is the Cemento-Enamel Junction (CEJ) which is the demarcation line between the crown and the root of the tooth. If the CEJ is covered by inflamed tissue or is below the gingival margin, for whatever reason, then the dentist must try to estimate the distance of the CEJ below the gingival margin to provide the reference. The gingival margin itself is not satisfactory as a reference because it is not a constant. It may recede or be swollen and inflamed. Likewise, the crown of the tooth is subject to wear, accident and reconstruction and is, therefore, an unreliable reference for a measurement that must be repeated at intervals over sometimes long periods of time. The taking of these measurements is complicated by a number of factors. The depth of the pocket must be determined by feel. Measuring the pocket at only selected spots around the tooth may miss a narrow pocket completely. Frequently, the CEJ must be found by feel, which depends on the existence of a "step" in the surface contour at the CEJ. Given human variability, this is probably not always going to be present. If a restoration is present that obliterates the CEJ, good dental practice is to eliminate any "step", if possible, as a potential home for bacteria. There has been an automated, constant force, CEJ finder probe produced experimentally at the University of Alabama, which looks for the presence of a "step". It then computes the provable location of the CEJ using acceleration and velocity data along the path of movement of the probe. This system is as invasive as a conventional probe and produces, at best, only a probable location for the CEJ. There also is on the market a device known as the "Florida Probe". This device uses a calibrated spring on a swing arm arrangement to measure the depth of penetration of a mechanical probe relative to the gingival margin. The data output by the device is recorded on a computer and printed out on a preprinted chart. The device is straight-forward but still invasive and uses an unreliable reference point. There have been other attempts to build constant force probes. None of these have gained wide acceptance in the dental community for various reasons.

SUMMARY OF THE INVENTION

It is an object of the present invention to provide a diagnostic mapping system for making and recording differential measurements of periodontal structures of a dental patient, in a minimally invasive manner.

Another object of the present invention is to provide a system for differential measurement and mapping of the upper boundary relative of the periodontal ligament of each tooth of a dental patient to a fixed point, the CEJ, as an indicator of the presence of periodontal disease.

Another object of the present invention is to provide a system for measuring and mapping all periodontal structures of each tooth of a dental patient that minimizes dependency of manual skill to obtain accurate results.

A further object of the present invention is a handpiece operable by an examining dental practitioner that contains, and permits control of, active sensors for measuring and mapping periodontal structures of a dental patient.

Another object of the present invention is a combination handpiece operable by an examining dental practitioner, and connecting structure therefor, that measures and records a permanent record of periodontal structure measurements.

An additional object of the present invention is a measuring and mapping system for use in diagnostic periodontal procedures that provides improved repeatability and automated record keeping.

Another object of the present invention is a process for digital measurement, recording, analyzing, comparing with previous measurements, video displaying and data storage of periodontal data for a dental patient.

Still another object of the present invention is a process for differential measurement and mapping of periodontal structures of a dental patient.

Another object of the present invention is an accurate, consistent, rapid, and relatively painless, system for obtaining periodontal data for a dental patient.

According to the present invention, the foregoing and additional objects are attained in one aspect of the present invention by providing a handpiece for an examining dentist having a vertically oriented, linear movement to identify and locate the Cemento-Enamel Junction (CEJ) of a specific tooth, at the point where the enamel of the crown and the cementum of the root of the tooth come together, and an ultrasonic pulse echo scanner to image and measure the depth of the periodontal pocket and the level of attachment of the periodontal ligament, both relative to the CEJ. The linear movement preferentially carries a small, ultrasonic transducer mounted at the distal end of a thin (<0.5 mm) flexible, polystyrene, probe through which it transmits and receives acoustic pulses to interrogate the surface of the tooth. The system detects differences between the material composing the enamel of the crown of the tooth and the material composing the root of the tooth. As the movement carries the tip of the probe across the boundary between the enamel and the cementum, the abrupt change in signal characteristics produces a state change in a toggle circuit to indicate the transition point. The accuracy of the measurement is a function of the step size of the linear movement driver. If the circumstance is such that the CEJ is obliterated at the chosen point by a restoration, crown, or other artifact, the system can compare the signal characteristics of the interrogated material and compare them to values stored in a solid state "look-up" table. The boundary of the artifact is then identified in the manner described above and used as the reference point. The linear movement is in fixed, known, geometric relationship to a second ultrasonic transducer operating at a frequency in the range of 15–25 MHz. This second, high frequency ultrasonic transducer is used to scan the periodontal pocket and the periodontal structures adjacent to, or abutting the surface of, the tooth root. The scanning ultrasonic transducer is mounted within the tip of the handpiece and communicates with the oral structures via a small aperture at the apex of that tip. The CEJ finder probe is normally retracted into a position adjacent to the scanning transducer and, when extended, passes through the same aperture that the ultrasound scan will subsequently pass through.

To activate the system, the tip of the handpiece is placed against the side of the tooth at the gingival margin, unless there has been substantial gum recession, in which case the tip is placed on the surface of the tooth slightly above the CEJ. After the tip of the handpiece is placed at the point of interest and the tooth identification number and the location point are entered via the control system, the scan is activated by the dentist practitioner. The linear movement then slides the tip of the CEJ detection probe from its retracted position, out through the aperture and down along the surface of the tooth while the CEJ finder ultrasound transducer emits a continuous series of interrogating pulses which travel down the flexible probe and into the surface of the tooth at the probe tip. The handpiece tip is spring urged against the surface of the tooth by virtue of the shape, material and path of the CEJ detection probe.

The movement of the probe is controlled by a feedback control system to find the CEJ. Such systems are well known and can be implemented in software. The position of the tip is measured by a highly accurate position sensor on the movement. A number of commercial systems offer accuracies that fall in the desired range. The location of the identified CEJ is returned to the movement control system, and to the data analysis system for use as a factor in the measurement calculation. After the CEJ location is transmitted to the data analysis system, the CEJ finder probe is withdrawn into its rest position. The scanning ultrasound transducer then transmits a short pulse of sound wave at a frequency in the range of 15–25 MHz through a water filled, frusto-conical extension housed within the tip of the handpiece. The function of this extension is three-fold: The water within the extension offers a low acoustic impedance path for the ultrasound pulse to pass into the periodontal pocket; the shape of the extension resizes the ultrasound beam from a nominal 0.24 inches at the transducer face to approximately 0.5 mm at the aperture; and, water forced in a stream from the aperture of the extension floods the contact area and the periodontal pocket with water to ensure that there are no voids or air bubbles in the path of the ultrasound beam. Ultrasound of this high frequency will not pass through air.

The water is continuously resupplied through a pressure regulating connection to the standard water supply available in all dental offices.

Because the ultrasound beam diameter is of approximately the same size as the periodontal space, it can pass into that space with minimal loss. Minimal loss is important as the actual energy content of the beam is very low. The materials and structures filling the periodontal space represent an area of relatively lower acoustic impedance between the much harder materials composing the tooth and wall of the bony pocket. The periodontal space will act therefore, somewhat as an acoustic wave guide which helps the acoustic wave follow the curved surface of the tooth root. The denser tissue (relative to the contents of the periodontal pocket) of the epithelium at the bottom of the periodontal pocket, and the still denser fibers of the actual periodontal ligament located below the epithelium, will reflect echoes back to the source transducer. The geometries involved, the frequency and the size of the beam act together to make the bony pocket, which is not of interest for the desired measurement, an extremely poor ultrasonic reflector in this procedure. This reduces to an absolute minimum any intrusion of the bony pocket into the field of view of the system of the present invention.

The speed of the acoustic wave in tissue and in water is a known constant. Therefore, the distance from the ultrasound transducer to the structure of interest is simply the time of flight in microseconds, times the velocity for tissue in mm per microseconds, divided by 2 (the time for the acoustic pulse to get to the structure of interest and the time for the echo to return). Since the distance between the ultrasound transducer and the CEJ has been derived in the previous step, the distance (or probing depth) to the structures of interest is the difference between those two measurements.

If desired, the CEJ locating operation can be repeated for verification. The values will be displayed to the operating physician, and upon acceptance will be automatically assigned to the location on the correct tooth and recorded in the patient records. The archived patient records have the capability of accepting annotation at any time, including post procedure.

The signal analysis and display software will produce a two-dimensional image with color coding and distance data superimposed for the dentist to use in making the diagnosis. Automatic archiving and retrieval of patient data for tracking and comparison purposes are also provided.

After the operating physician gains some skill with the use of the system, he/she should be able to do a quick scan by sliding the probe tip along the gingival margin, taking data continuously, without deploying the CEJ finder. As long as no pocket below the nominal depth is observed then there should be no need for further attention. If a suspicious area is located, then the full cycle can be run. This type of operation would speed up a periodontal scan dramatically, as well as applying the absolute minimum of discomfort to the patient. These virtues would make for increased patient acceptance of the procedure, and greater throughput of patients for the dentist. Coupled with increased accuracy over time and automated record keeping, the set of system capabilities represents a distinct improvement in the state of the art.

As an alternative methodology for finding the CEJ, the CEJ finder probe can be fitted with an optical interrogation system. The optical system operates in a completely analogous manner to the acoustic system, but uses different material properties. The material interrogation and boundary detection can be accomplished by the use of a fiber optic pickup which would be mounted in the same manner as described above on the linear movement. The fiber optic pickup interrogates the material with illumination from two (2) laser diodes at two (2) selected frequencies. The enamel of the crown reflects more energy at frequency 1 that at frequency 2, with the converse being true on the cementum of the root. The reflected laser light is detected by two (2) optical pickups which are individually selected and tuned to frequency 1 and frequency 2. The outputs of the optical pickups undergo a state change at the transition point. It is possible to use a look-up table to provide sensitivity to restoration material in this scheme as well.

BRIEF DESCRIPTION OF THE DRAWINGS

A more complete appreciation of the invention and many of the attendant advantages thereof will be more readily appreciated when considered with the detailed description and the accompanying drawings, wherein.

DETAILED DESCRIPTION

Figure 1:
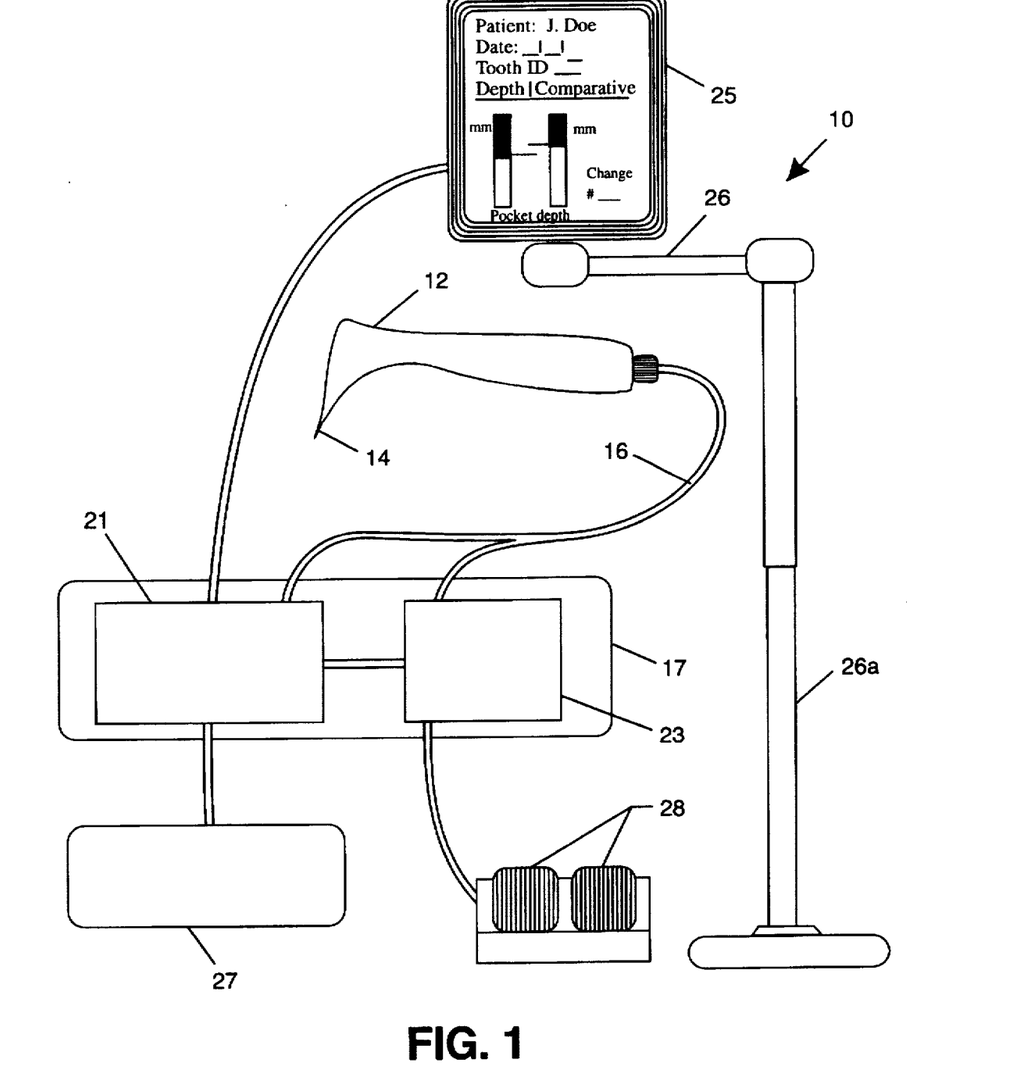
FIG. 1 is a schematic illustration of the periodontal mapping system of the present invention.

Referring now to the drawings and more particularly to FIG. 1, the differential measurement periodontal structures mapping system of the present invention is schematically shown and designated generally by reference numeral 10. Mapping system 10 includes a handpiece 12 having a sensor probe 14, under the control of a linear movement, extending from a first end thereof. The sensor probe 14 is linearly movable relative to the housing of handpiece 12, and the details of which will be more fully described hereinafter. The second end of handpiece 12 is connected via cable 16 through a first chassis 17 to a control computer 23 and an analysis subsystem 21. Control computer 23, connected to a suitable power supply (not shown), and housed in first chassis 17, controls the operation for movement of sensor probe 14 and for the operation of analysis subsystem 21. Power for operation of control computer 23 is provided by a conventional AC or DC power supply.

A small display 25, attached on an adjustable arm 26, which can be mounted to the dental chair, or to a movable support 26a, is in operative connection with the optical analysis subsystem 21, as will be further explained hereinafter. A data storage system 27 is in connection with analysis subsystem 21, as will also be further explained hereinafter. Conventional foot pedal controls 28 are provided for controlling the operation of the mapping system 10.

As schematically shown in FIG. 1, the signal analysis and display software will produce a two-dimensional, bar graph type image on display 25. The bar graph will give depth in 1/10th mm increments. If the scan is of a previously scanned patient, the previous scan will be displayed together with the delta change. Each frame has the relevant patient data as a header.

Figure 2:
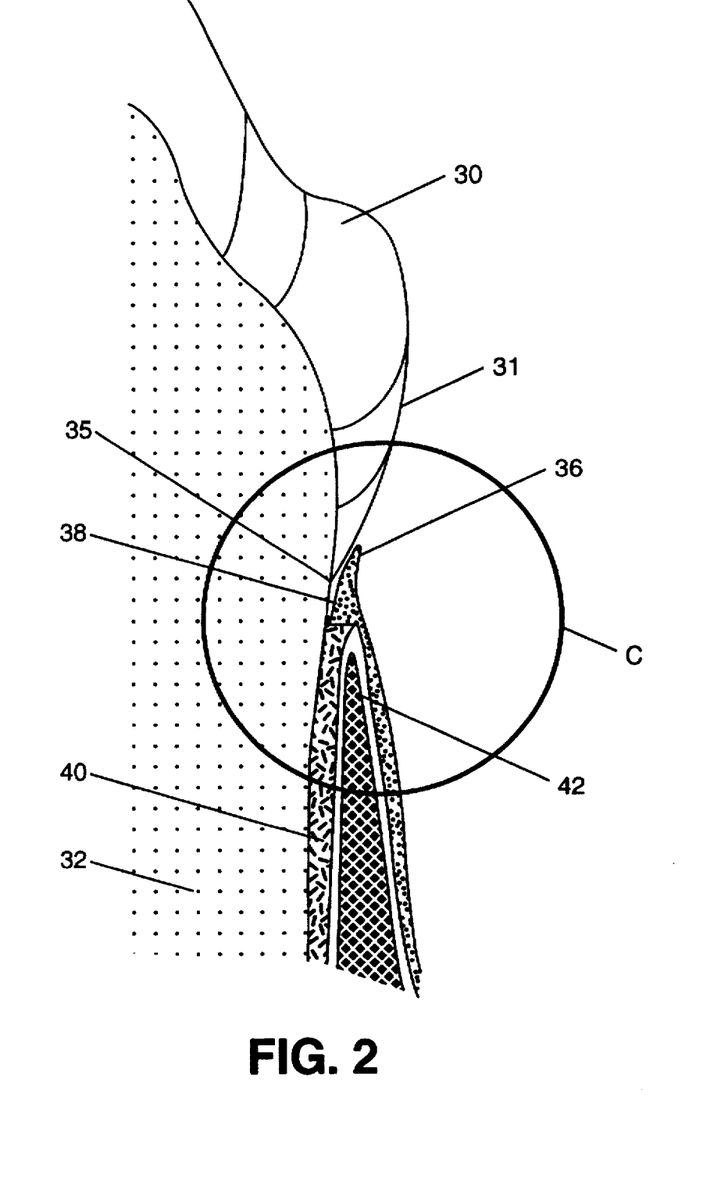
FIG. 2 is a part schematic, part sectional, illustration of a normal human tooth and periodontal structures.

Changes in the differential measurements will be visible and measurable over a time interval where periodontal disease is present, and will give an indication, and the rate of progress of the disease. Referring to FIG. 2, these changes will be caused by recession of the gum tissue 36, loss of attachment of the periodontal ligament 40 and finally, erosion of the bony pocket that supports the tooth in the jaw bone 42. Differential measurements are normally obtained at three spaced intervals on the front and back of each tooth, as well as between the teeth.

Referring now more particularly to FIG. 2, there is shown an enlargement of a portion of a human tooth, designated by reference numeral 30, and showing a portion of the enamel surface 31 of the tooth crown. The root of tooth 30 is designated by reference numeral 32. The location of the point where the enamel 31 of the tooth crown and the cementum surface of the tooth root 32 come together is referred to as the Cemento-Enamel-Junction (CEJ) of the tooth, and is designated by reference numeral 35. The CEJ for a healthy mouth, that is, one essentially free of periodontal disease, is normally located at, or slightly below, the top of the tooth gum 36. This gum line is termed the gingival margin of the tooth. The area or spacing between the gum (gingiva) 36 and the root 32 of a tooth 30 is called the periodontal pocket, and is designated by reference numeral 38. The bottom of periodontal pocket 38 is separated from the periodontal ligament 40 by a covering of epithelial tissue 36, which is contiguous with the inner surface of the periodontal pocket 38. The periodontal ligament 40 normally covers the entire surface of the tooth root 32 and both separates the root 32 from, and attaches it to, the jaw bone 42.

Circled area "C" in FIG. 2 represents the general area of an individual tooth 30 that is mapped by the present invention to determine the presence of, and/or the change in the attachment level of the periodontal ligament 40 and the depth of the periodontal pocket 38 as a marker, for periodontal disease.

Figure 3:
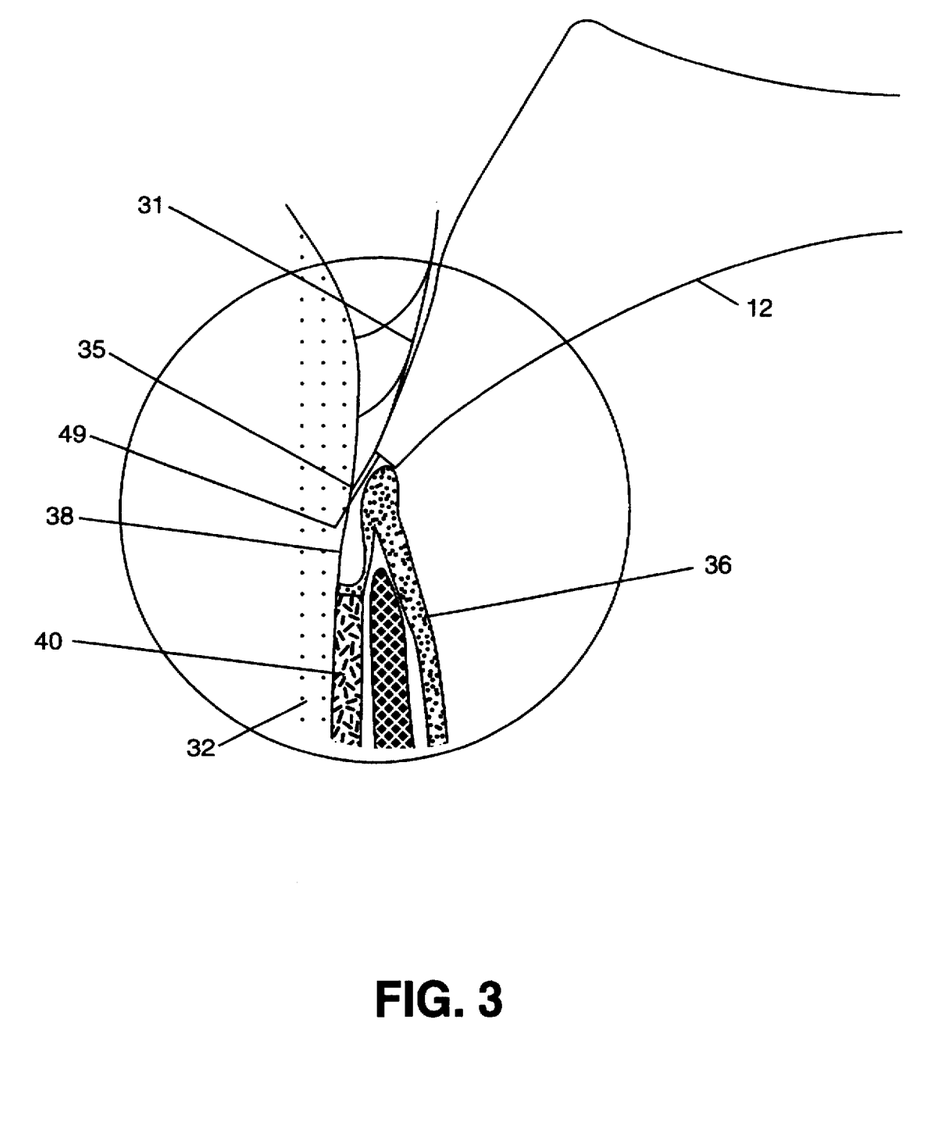
FIG. 3 is a schematic view of a portion of the circled area designated "C" of FIG. 2 with the handpiece of the mapping system of the present invention in position for making measurements.

Referring now more particularly to FIG. 3, an enlarged view of the circled area "C" in FIG. 2, is illustrated. As shown therein, the open tip 49, at the distal end, of handpiece 12 is positioned against the gingival margin, (gum line) 36 of the tooth 30 to be examined. The tooth identification number is entered, via the control system, into the data storage system 27 (FIG. 1), as is the location of the point to be probed.

Figure 4:
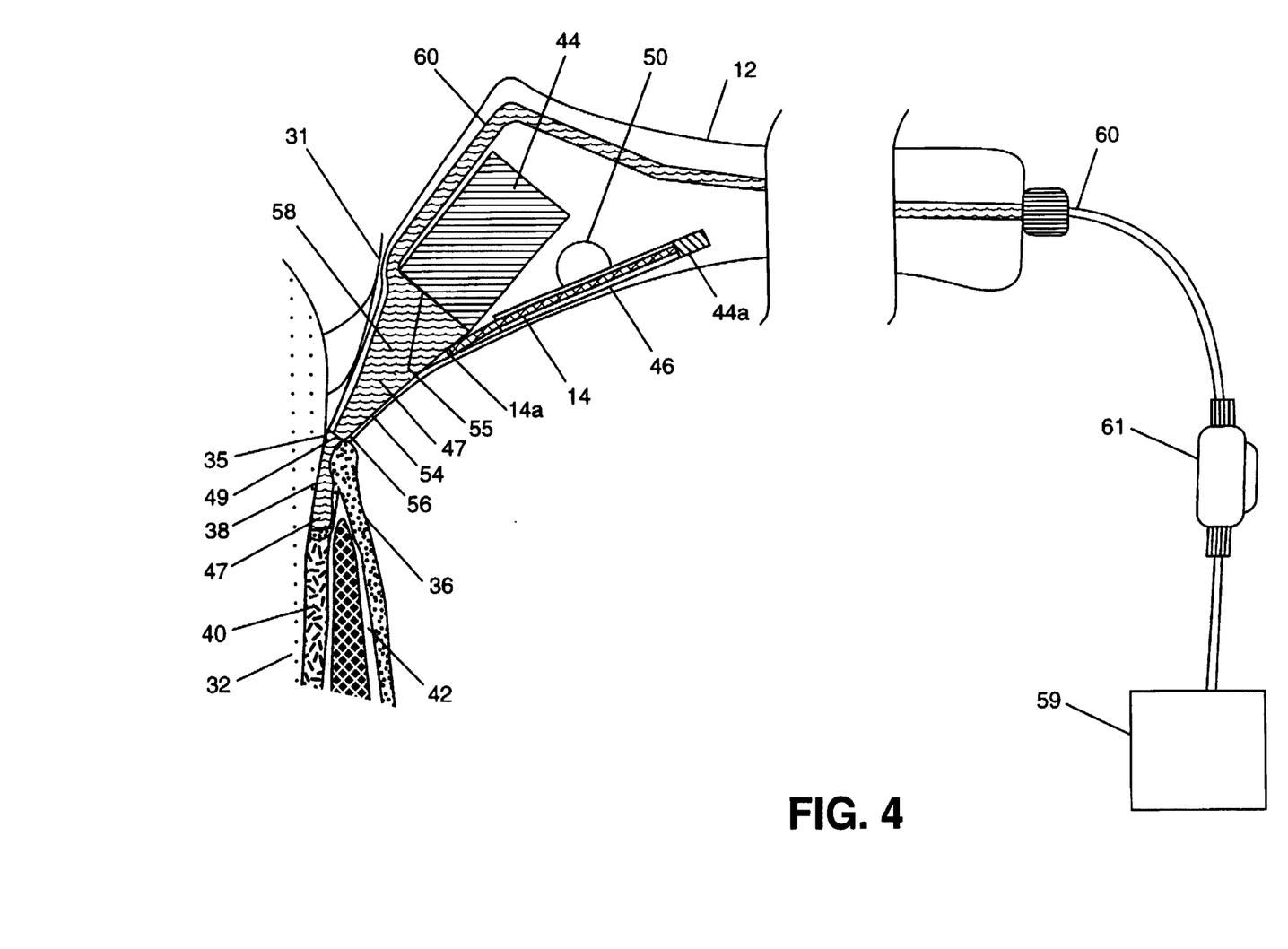
FIG. 4 is a schematic view similar to FIG. 3, with the handpiece having portions shown in section to show the components contained therein, and the handpiece tip placed against the gingival margin and flooding the periodontal pocket with water.

Referring now more particularly to FIG. 4, the scanning ultrasound transducer 44 is shown within handpiece 12 in adjacent relationship to the linear movement 46 which drives the CEJ finder probe 14, from the retracted position shown to an extended position, as will be further explained hereinafter. Another ultrasonic transducer 44a is carried by linear movement structure 46 to transmit ultrasonic sound waves through sensor probe 14, as will be further explained hereinafter.

Ultrasound transducer 44, is within the frequency range of 15–25 MHz and, in the preferred embodiment is a 20 MHz high frequency ultrasonic transducer. Ultrasonic transducer 44a is in the frequency range of 2–5 MHz, and preferably 5 MHz. A hollow frusto-conical extension 54 is provided extending from ultrasonic transducer 44. Extension 54 includes a base portion 55 secured to the transmitting end of transducer 44, and an apex 56 terminating adjacent the open tip end 49 of handpiece. The lumen 58 of extension 54, and the periodontal pocket 38 are flooded with water 47. The extension lumen 58 is connected to a water source 59, available in all dental offices, to provide a constant flow of water through a suitable conduit 60. Water is continuously resupplied through a pressure regulating connection 61 disposed in conduit 60. The water flow fills extension lumen 58 and exits through the distal opening 49 of handpiece 12. Since ultrasound at these high frequencies will not pass through air, water 47 is employed to serve as a medium through which the ultrasound pulses from the ultrasound transducer 44 can travel. Water 47 also serves as a couplant between the open tip 49 of handpiece 12 and the gingival tissue 36.

The pressurized water within extension 54 offers a low impedance path for the ultrasonic pulses from transducer 44 to pass into the periodontal pocket 38. Also, the frusto-conical shape of extension 54 resizes the ultrasonic beam produced by transducer 44 from an approximately 0.24 inch diameter at the transducer face to approximately 0.5 mm at the apex 56. Water 47 is forced as a stream from the opening 49 of handpiece 12 to flood the contact area and periodontal pocket 38 to ensure that there are no voids or air bubbles in the path of the ultrasonic beam.

If the periodontal pocket 38 is large, water 47 from the extension lumen 58 will fill it to provide passage for the ultrasound pulses to the bottom of the periodontal pocket 38 and, hence the periodontal ligament 40.

Figure 5:
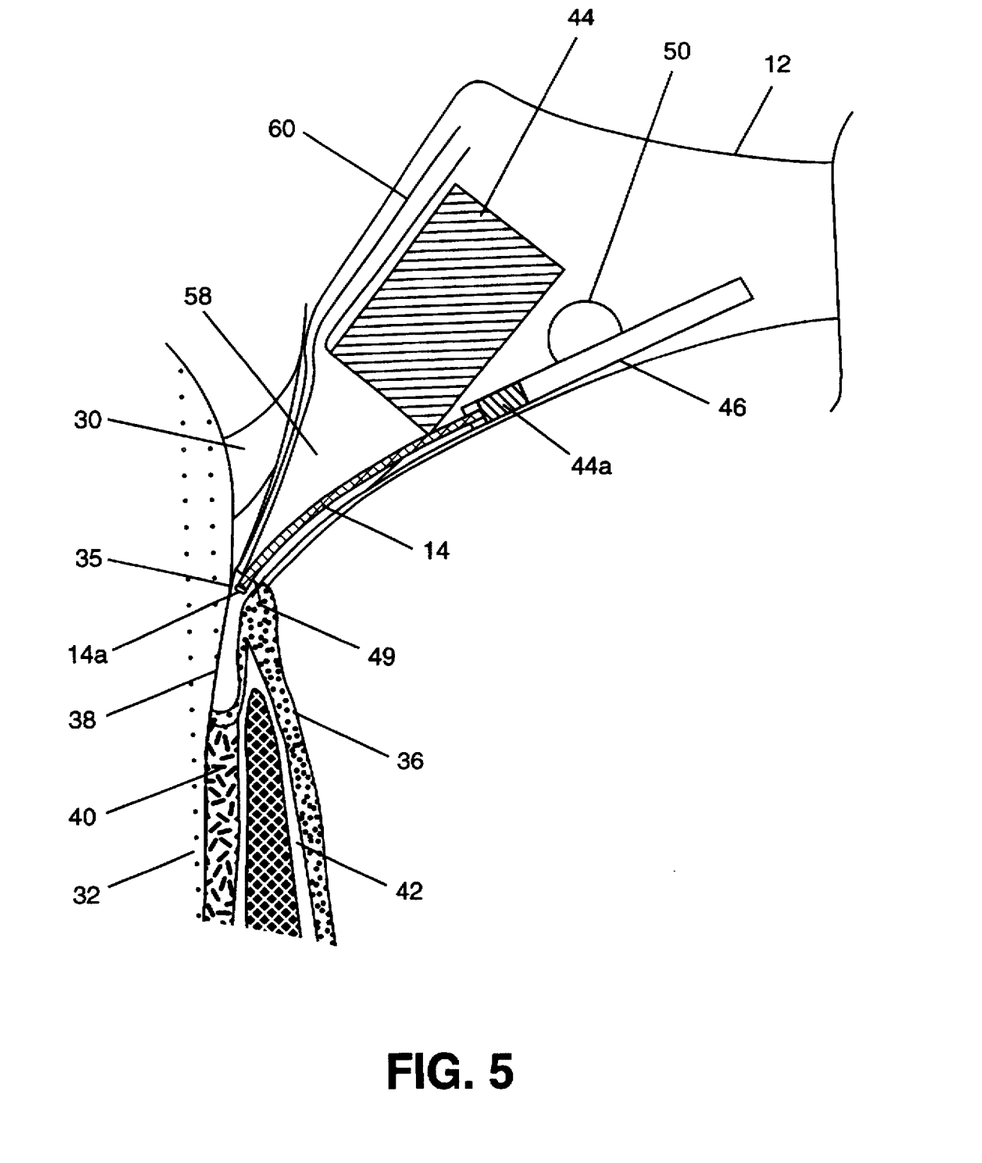
FIG. 5 is a schematic view similar to FIG. 4 (with parts omitted) and illustrating the CEJ finder probe extended into the lumen and out of the aperture along the surface of the tooth.

Referring now more particularly to FIG. 5, further details of the handpiece 12 and the sensing end 14a of the CEJ sensor probe 14 is illustrated. In the interest of clarity and brevity, water supply 59, conduit 60 and pressure regulator connector 61 are omitted in FIG. 5. As shown therein, sensor probe 14 is shown in position to sense the location of the CEJ 35 of a specific tooth 30. The CEJ probe 14 has been advanced by the linear movement 46 out of its resting place, through the extension lumen 58, out of the tip aperture 49, and along the surface of the tooth 30, towards the CEJ 35. The surface passed over is continuously interrogated. Sensor probe 14 is formed of any suitable flexible material that transmits ultrasonic sound waves. In a specific embodiment sensor probe 14 was formed of slightly less that 0.5 mm diameter polystyrene plastic stock. Other suitable plastic or composite materials that readily transmit ultrasonic sound may be employed for this purpose.

The movement of probe 14 is controlled by a feedback, control system to find the CEJ 35 by looking for the difference in material characteristics on either side of that line of demarcation. If the area of the tooth 30 to be inspected has a restoration, the material characteristics of the restorative material are available to the control system via a "look-up table" in system memory that has previously been loaded with the relevant characteristics of different types of restorative materials. The operator selects a material from a list and the control system uses that value, looking for the crossover point to the known value for the cementum of the tooth root. The position of tip 14a of probe 14 is measured by a highly accurate position sensor 50 which is incorporated into the linear movement 46. The determined, relative location of the CEJ 35 is returned to the control subsystem 21 and to the data analysis and display computer 27. For the desired degree of accuracy, a commercial Linear Variable Displacement Transducer is employed, or alternatively, a stepper motor/encoder could be employed to drive the movement and supply a measurement output. There are several types of available commercial linear movements that can be used for this process.

Figure 6:
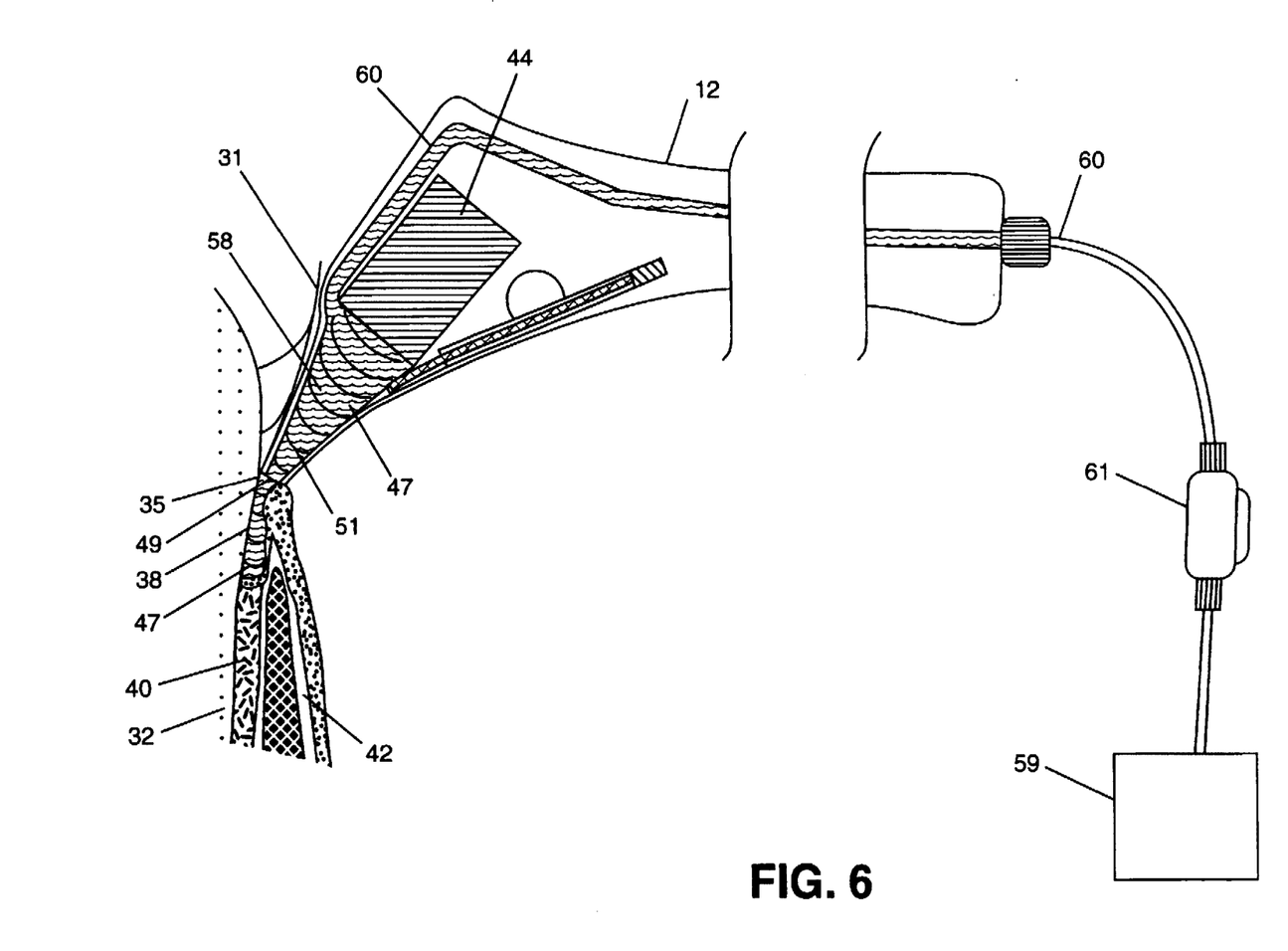
FIG. 6 is a schematic view similar to FIG. 5 with the CEJ finder probe retracted and illustrating the sound pulses traveling from the ultrasound transducer down through the periodontal pocket to the top of the periodontal ligament.

Referring now to FIG. 6, the CEJ sensor probe 14 is shown withdrawn back into the side of the lumen 45 and the ultrasonic transducer 44 is pulsing. When the CEJ 35 has been located by the CEJ finder 14, a trigger pulse is sent to the data analysis subsystem 21. As a result of this stimulus the ultrasonic transducer 44 transmits a pulse of sound waves at a frequency of 20 MHz into the water filled lumen 58. The produced sound wave 51 travels down through the lumen 58, out of the distal opening 49, and is coupled into the gingival margin. The sound wave 51 continues to travel down through the periodontal space, traversing the periodontal pocket 38, and passing through the epithelial tissue 36 at the bottom of the pocket. Some of the sound is reflected from the epithelial tissue 36 and some will pass through and be reflected from the top of the periodontal ligament 40.

It is to be noted that, if there has been gum recession to the point that the CEJ is exposed, the tip of the handpiece 12 must be placed slightly above CEJ 35 in order for the CEJ finder probe 14 to perform properly. Water is forced from the opening 49 of the lumen 58 with sufficient force to flow along the tooth surface and flood the gingival margin, thus providing a path for the ultrasound pulses. This technique is common in industrial ultrasound inspection systems where it is known as a "squirter" system.

It should also be noted that the sequence can be reversed, scanning the pocket first and then finding the CEJ. In that sequence the tip of the handpiece 12 is moved laterally along the gingival margin of each tooth 30, pulsing continuously from ultrasonic transducer 44, until a pocket of deeper than nominal depth is detected. At that time, the CEJ finder 14 can be deployed to accurately measure the differential depth of the detected periodontal attachment loss.

Figure 7:
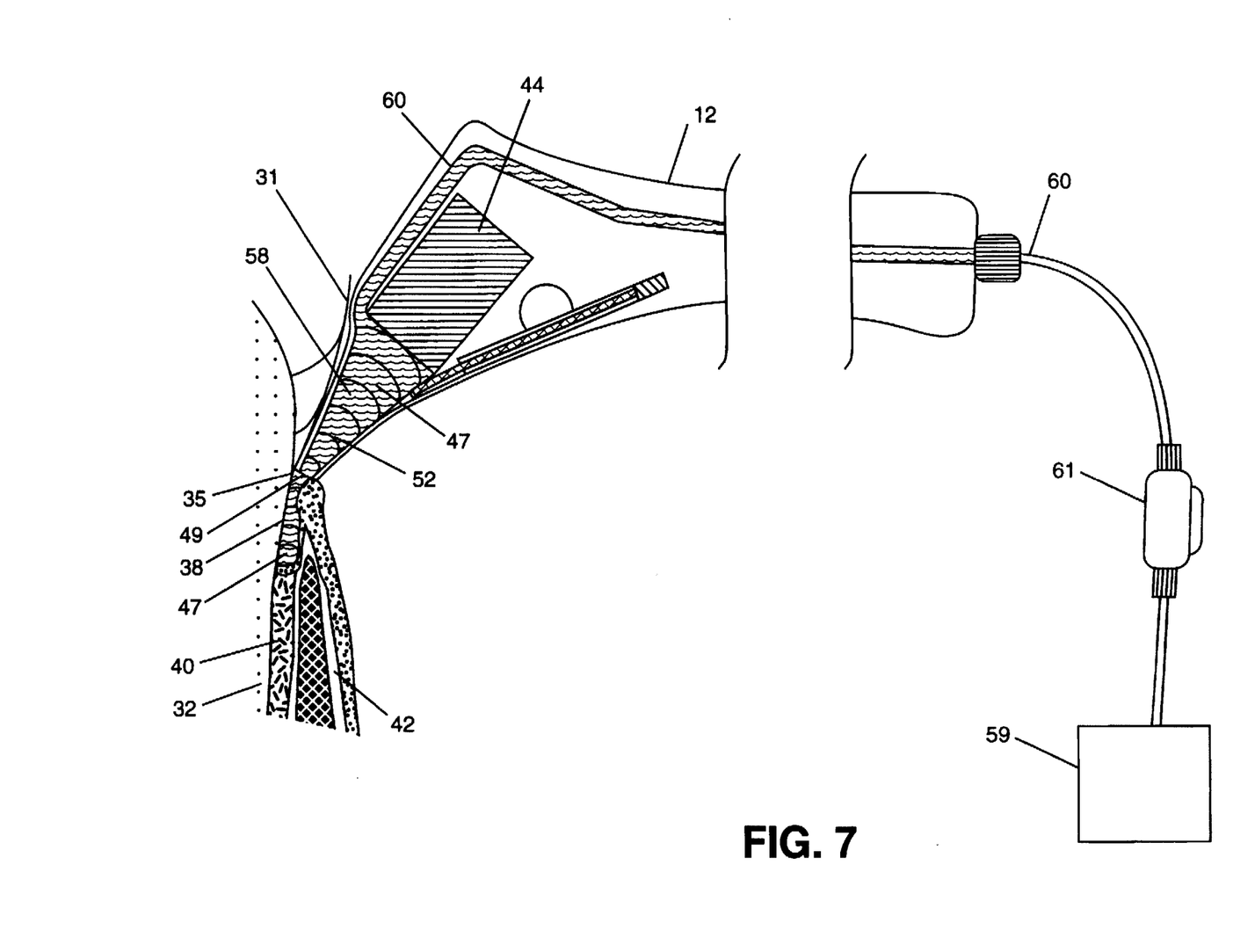
FIG. 7 is a schematic view of the echoes from the bottom of the pocket and the top of the periodontal ligament returning to the ultrasound transducer.

Referring now to FIG. 7, the returning echoes 52 from the structures of interest are shown returning to the transducer 44 through the periodontal pocket 38 and the water filled lumen 58. As illustrated therein, the sound waves 52 that have been reflected from the structures of interest will travel back through the pocket 38 and the water filled lumen 58 of extension 54 and be detected when they arrive at the surface of the ultrasonic transducer 44.

Figure 8A:
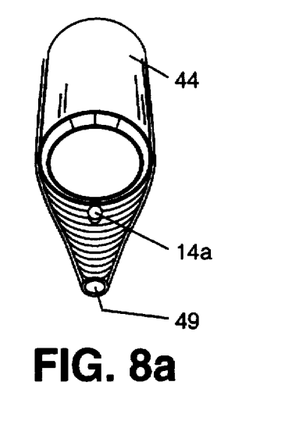
FIG. 8a, b, c, and d are schematic view details of the movement of the CEJ finder probe out of the rest position, through the lumen and out of the tip aperture of the handpiece.

Referring now to FIG. 8a, there is shown a perspective view of the interior of the lumen 58 illustrating the face of the ultrasound scanning transducer 44, and tip 14a of the CEJ finder probe 14 being shown in the retracted or rest position in the side of the frusto-conical extension 54.

Figure 8B:
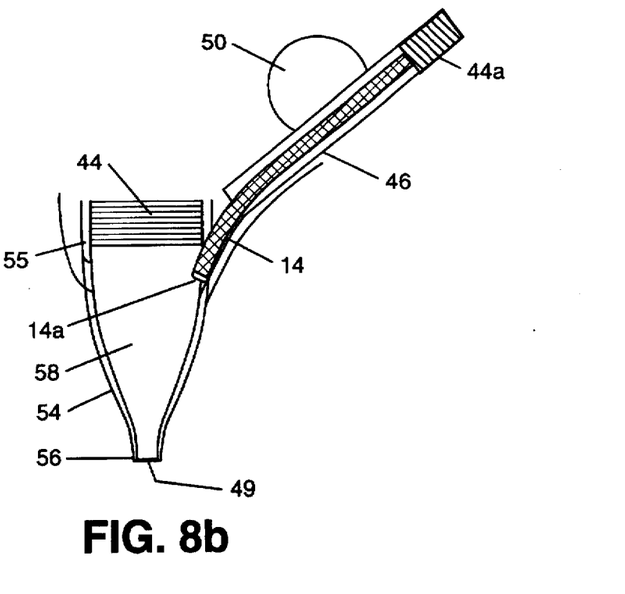

FIG. 8b is a side schematic view of the structure shown in FIG. 8a and more clearly showing the CEJ probe 14 in the fully retracted position.

Figures 8C, 8D:
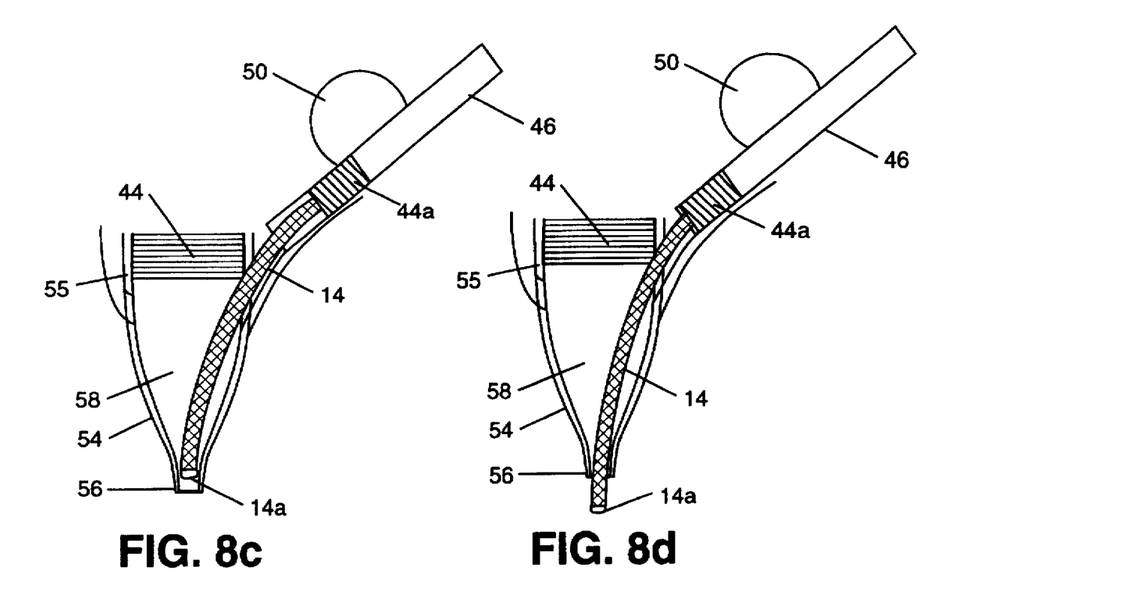

FIG. 8c is similar to FIG. 8b and shows the CEJ finder probe 14 partially extended.

FIG. 8d is similar to FIG. 8c and shows the CEJ finder probe 14 extended through the tip aperture 49 of handpiece 12 and extension 54.

Figure 9:
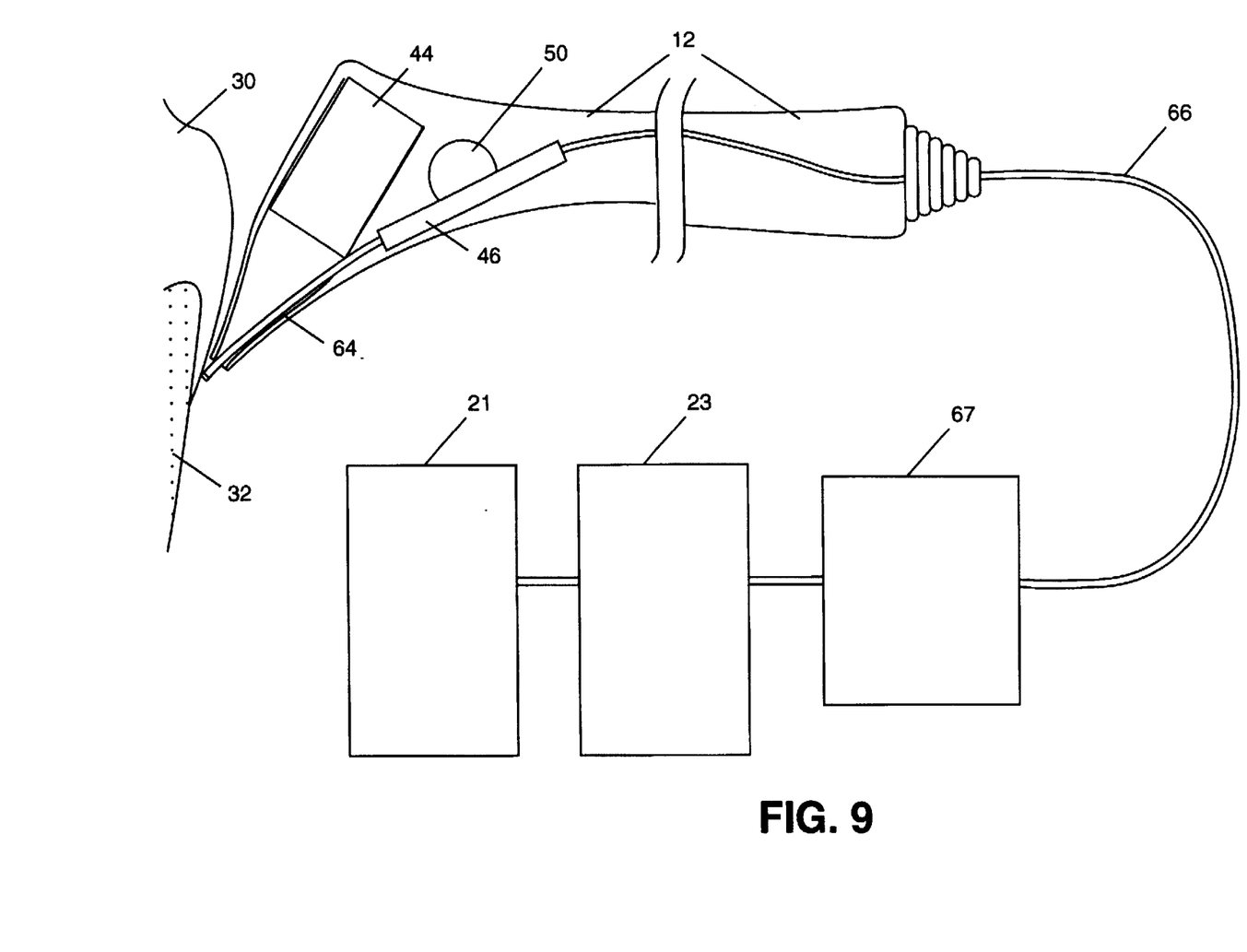
FIG. 9 is a schematic view of part of the mapping system of the present invention when employing a fiber optic CEJ sensor and the optical subsystem interrogator therefor.

Referring now to FIG. 9, an alternate embodiment for the CEJ finder probe is illustrated. In this embodiment, ultrasonic sensor probe 14 is replaced by a fiber optic sensor probe 64. Also, ultrasonic transducer 44a is omitted. This embodiment operates in a completely analogous manner to the acoustic system, but uses different material properties. The fiber optic sensor probe 64 is movable, by linear movement structure 46, from a retracted position within headpiece 12 to an extended position to contact and find the CEJ of a tooth.

Fiber optic probe 64 interrogates the material with illumination from two laser diodes at two selected frequencies. The enamel of the crown reflects more energy at a first frequency that at the second frequency, with the converse being true on the cementum of the root. The reflected laser light is detected by two optical pickups contained within an optical subsystem 67, which are individually selected and tuned to the first and second frequencies. The reflected laser light is transmitted by a fiber optic cable 66 from the sensor 64 to optical subsystem 67. The outputs of the optical pickups undergo a state change at the transition point in the optical subsystem to convert the signal to a digital mode. The digital signal is transmitted through computer control subsystem 23 to the analysis and display computer 21, as in the previously described embodiments. Look-up tables to provide sensitivity to restoration materials may also be employed with this embodiment of the invention.

It is thus seen that the present invention provides a system that eliminates, or at least minimizes, some of the sources of inaccuracies inherent in the standard procedure now employed for detecting and evaluating periodontal disease. The present invention provides more and better diagnostic information to the physician, in a very user friendly manner. The accuracy, and repeatability obtained by the present invention, will be improved to the point that it could provide a "gold standard" for periodontal measurements.

Although the invention has been described in reference to specific embodiments thereof, it is not so limited, and variations thereof will be readily apparent to those skilled in the art in the light of the above teachings. For example, although the specific embodiments described herein are restricted to a two dimensional system, the mounting of a sectored, as opposed to a simplex, ultrasound transducer as the depth scanning element would permit the formation of a narrow angle sector scan. That data could then be processed to give a real time image of the periodontal area with a much richer information content. Such an image would provide the dentist practitioner with a more comprehensive picture of the actual conditions within the periodontal area and thus the possibility of more accurate diagnosis in the presence of complications. The richer information content could also permit the use of the present invention as a resource for the diagnosis of other conditions, oral and otherwise.

Again, it appears possible to do direct video imaging within the periodontal pocket so that the physician may visually evaluate the on-site conditions from the magnified image provided on the display screen of the data analysis computer.

Thus, it is to be understood that the specific embodiments described herein are to be deemed as exemplary only and are not exhaustive. Where specific materials are mentioned, it is to be understood that these specific examples are given as illustrative purposes only and are not to be deemed as requirements. Any material having the structural and chemical properties needed to perform the intended functions are considered to be operative in practice of the present invention. These, and other and various modifications and variations of the invention will, accordingly, be readily apparent to those skilled in the art in the light of the above teachings. It is therefore to be understood that, within the scope of the appended claims, the invention may be practiced other than as specifically described herein.

What is claimed as new and desired to be secured by Letters Patent of the United States is:

1. A diagnostic mapping system for making and recording differential measurements of periodontal structures of a dental patient comprising, in combination:

a dental handpiece having a first and a second end and, adapted to be controllably placed by a dentist at the points of interest along the gingival margin of each tooth of a patient;

first and second acoustic sensors disposed within an open, tapered tip of said first end of said handpiece;

first and second ultrasonic transducers for said respective first and second acoustic sensors contained within said handpiece;

said first ultrasonic transducer being disposed in fixed spaced relationship with said open, tapered tip of said handpiece;

said second acoustic sensor being a sensor probe and linearly movable from a retracted position completely within said handpiece to an extended position where a portion of said second acoustic sensor probe extends from said handpiece;

a control computer in operative connection with said second end of said handpiece;

means connected to said control computer to effect linear movement of said second acoustic sensor;

means connected to said control computer and to said second end of said handpiece for receiving and analyzing output from said first and said second acoustic sensors; and means for receiving, displaying, and storage of the analyzed data for further study and comparison with previous and subsequently obtained data.

2. The diagnostic mapping system of claim 1 including a substantially frusto-conical coupler housing;

said coupler housing having a base end extending from said first ultrasonic transducer and an open apex end leading, and disposed adjacent, to said open tapered tip of said handpiece;

a pressurized water supply in fluid communication with said coupler housing and serving to selectively flood the lumen thereof with pressurized water.

3. The diagnostic mapping system of claim 2 wherein said first acoustic sensor is a depth measuring sensor for measuring the depth of the periodontal pocket of an individual tooth and the periodontal ligament distance relative to the cemento-enamel junction; and, wherein said pressurized water flooding the lumen of said coupler housing extends into and fills the periodontal pocket with a water flow of sufficient force to provide a continuous water medium path for the ultrasound pulses between said first ultrasonic transducer and the periodontal pocket bottom.

4. The diagnostic mapping system of claim 1 wherein said second acoustic sensor probe is a cemento-enamel-junction finder and includes a flexible, linearly movable, probe; a linear mechanical movement structure, in connection with and, serving to provide reciprocating linear movement for said second acoustic sensor probe; and said means connected to said control computer to effect linear movement of said second acoustic sensor including a drive system connected to said control computer and to said second end of said handpiece for said linear movement structure to effect linear movement of said second sensor probe.

5. The diagnostic mapping system of claim 1 wherein said means for receiving, displaying, and storage of the analyzed data for further study and comparison includes a display screen; mounting structure for said display screen including an adjustable arm support to permit location and positioning of said display screen for view of the patient and the dental practitioner.

6. The diagnostic mapping system of claim 5 wherein said display screen is a miniature video system connected to said control computer and serving to produce (1) a screen view of the patient identification; (2) current tooth number location of the tip of the handpiece during the procedure; (3) current control settings; (4) current function underway; (5) a graduated, bar graph type display of the instantaneous pocket dept detected by the instrument; (6) cemento-enamel-junction location; (7) digital display of the cemento-enamel-junction to periodontal ligament distance, (8) aligned duplicate bar graph display of archived data for that patient, if available, together with the delta change in attachment level and the time interval since acquisition of the archived data; and (9) available command options which will return an indicator of which option is selected.

7. The diagnostic mapping system of claim 1 including foot control actuator means for said mapping system; said foot control actuator means being operable by the physician to thereby eliminate the requirement of the physician to look away from the patient to control the system during a mapping procedure.

8. The diagnostic mapping system of claim 1 wherein said first ultrasonic transducer operates at a frequency in the range of 15–20 MHz and said second ultrasonic transducer is disposed at the distal end of said sensor probe and operates at a frequency in the range of 2–5 MHz.

9. A diagnostic mapping system for making and recording differential measurements of periodontal structures of a dental patient comprising, in combination:

a dental handpiece having a first and a second end;

said dental handpiece being controllable, and adapted to be placed, by a dentist at the points of interest along the gingival margin of each tooth of a patient;

first and second sensor means disposed within an open tapered tip of said first end of said handpiece;

at least one of said first and said second sensors including a sensor probe;

said sensor probe being linearly movable from a retracted position completely within said handpiece to an extended position for making contact with a point of interest on a tooth of a patient;

a control computer in operative connection with said second end of said handpiece;

means connected to said control computer to effect linear movement of said sensor probe;

means connected to said control computer and to said second end of said handpiece for receiving and analyzing output from said first and said second sensors; and means for receiving, displaying, and storage of the analyzed data for further study and comparison with previous and subsequently obtained data.

10. The diagnostic mapping system of claim 9 wherein said first and said second sensor means comprise a pair of ultrasonic sensors and including a first ultrasonic transducer for said first sensor and a second ultrasonic transducer for said second sensor; each of said first and said second ultrasonic transducers being contained within said handpiece.

11. The diagnostic mapping system of claim 10 wherein said first sensor is a depth measuring sensor for measuring the depth of the periodontal pocket of an individual tooth and said first ultrasonic transducer for said first sensor including a hollow, frusto-conical, coupler extension having a base portion secured thereto and an apex terminating adjacent to said open tip of said handpiece.

12. The diagnostic mapping system of claim 11 including a source of pressurized water in fluid communication with said hollow, frusto-conical, coupler extension.

13. The diagnostic mapping system of claim 11 wherein said second sensor is a cemento-enamel junction finder and includes a flexible, linearly movable, probe and said means connected to said control computer to effect linear movement of said sensor probe includes linear movement structure to effect controlled reciprocating linear movement of said flexible linearly movable probe.

14. The diagnostic mapping system of claim 9 wherein said means for receiving, displaying, and storage of the analyzed data for further study and comparison includes a display screen; mounting structure for said display screen; said mounting structure including an adjustable arm support for said display screen to permit location of said display screen in view of the patient and the dental practitioner.

15. The diagnostic mapping system of claim 9 wherein said first and said second sensors comprise a cementoenamel-junction finder and a depth measurement sensor for measuring the depth of the periodontal pocket and the level of attachment of the periodontal ligament of the tooth being examined relative to the cemento-enamel-junction of the tooth.

16. The diagnostic mapping system of claim 15 wherein at least one of said sensor means is an optical fiber sensor.

17. The diagnostic mapping system of claim 16 including a fiber optic cable leading from said optical fiber sensor to an optical subsystem to convert the signal from said optical fiber sensor to a digital mode for transfer to said means for receiving and analyzing output from said first and said second sensors.

18. The diagnostic mapping system of claim 15 wherein said second sensor comprises a thin flexible probe having an approximate 0.5 mm thickness for transmitting and receiving acoustic pulses to interrogate the surface of a tooth.

19. The diagnostic mapping system of claim 15 wherein said first ultrasonic transducer for said depth measurement sensor has a frequency in the range of 15–20 MHz.

20. The diagnostic mapping system of claim 15 wherein said ultrasonic transducer for said cemento-enamel-junction finder has a frequency in the range of 2–5 MHz.

* * * * *